United States Patent [19]

Harris

[11] Patent Number: 4,788,986
[45] Date of Patent: Dec. 6, 1988

[54] HOLDER FOR BLOOD COLLECTING NEEDLE

[76] Inventor: Jim C. Harris, P.O. Box 391, New Albany, Ind. 47150

[21] Appl. No.: 26,201

[22] Filed: Mar. 16, 1987

[51] Int. Cl.$^4$ .............................................. A61B 5/00
[52] U.S. Cl. ................................... 128/763; 604/242; 604/272; 604/403
[58] Field of Search ...................... 128/763, 764, 770; 604/51, 52, 188, 204, 206, 240, 242, 272, 403, 411–415; 403/341, 348, 349, 353, 315

[56] References Cited

U.S. PATENT DOCUMENTS

| | | | |
|---|---|---|---|
| 1,019,657 | 3/1912 | Kerr | 403/349 |
| 1,667,273 | 4/1928 | Stewart | 604/240 |
| 1,742,497 | 1/1930 | Dickinson | 604/242 |
| 2,158,593 | 5/1939 | Scrimgeour | 604/242 |
| 2,169,371 | 8/1939 | Payne | 604/242 |
| 4,312,362 | 1/1982 | Kaufman | 127/763 |

*Primary Examiner*—Max Hindenburg
*Attorney, Agent, or Firm*—Woodard, Emhardt, Naughton, Moriarty & McNett

[57] ABSTRACT

A needle holder for use with a double ended blood collection needle having a first sharpened end and a second sharpened end and a hub intermediate the first and second ends of the needle, and an evacuated blood collection tube stoppered at one end by a rubber-like stopper. The needle holder includes a rotatable sleeve mounted on the needle hub holding end of the needle holder. The sleeve has an end wall adjacent the end wall of the needle holder, the end wall of the sleeve defining an oval aperture therethrough. The end wall of the needle holder defines a recess for receiving the needle hub so as to prevent rotation of the needle hub with respect to the needle holder. As the sleeve is rotated with respect to the needle holder, portions of the end wall of the sleeve adjacent the oval aperture are caused to overlie portions of the needle hub, thereby preventing axial displacement of the needle with respect to the needle holder. This action is reversible by further rotation of the sleeve, or preferably, by reverse rotation of the sleeve back to its original orientation, thereby releasing the needle hub. One benefit is that a used needle can be disengaged from the needle holder without one's hand approaching the used end of the needle, thereby reducing the risk of sticking oneself with a contaminated needle.

4 Claims, 2 Drawing Sheets

HOLDER FOR BLOOD COLLECTING NEEDLE

BACKGROUND OF THE INVENTION

1. Field of the Invention

The present invention is generally related to devices for drawing blood samples from a human patient, and is more particularly related to such devices as employ a double-ended blood collection needle in which one end of the needle is inserted hypodermically into the blood vessel, and the other end of the needle pierces the stopper of an evacuated blood-collection tube, whereby the blood is drawn through the needle into the blood-collection tube.

2. Description of the Related Art

A popular method and apparatus currently in use for drawing blood samples includes essentially three separate components. The first component is an evacuated blood-collection tube, generally shaped like a chemist's test tube and having the open end sealed with a stopper of rubber or a rubber-like material. The blood collection tube is supplied pre-evacuated and with at least the interior surfaces of the tube and stopper sterilized. The tube is usually made of glass, and can be cleaned, autoclaved, evacuated and stoppered anew by the supplier, if desired, although the tube can also be disposed of after one use, as economics and good health care practice may dictate. The second component is a hollow blood-collection needle which is essentially a stainless steel cannula sharpened at both ends, with a hub of some sort bonded about the needle intermediate the two ends. As supplied, the hub is usually located off center with respect to the length of the needle, at a point closer to the end which is ultimately used to pierce the rubber stopper. Incidentally, the end used to pierce the rubber stopper, while having a beveled point, usually has the very tip of the beveled point bent over slightly toward the longitudinal axis of the needle. This construction allows the end of the needle to puncture the rubber stopper without cutting a rubber core plug which would obstruct the needle The hub of the blood collection needle can have flanges which extend radially outwardly perpendicular to the needle, or screw threads on its outer surface, depending upon the particular manufacturer's chosen design. In either case, the flanges or screw threads have the purpose of engaging and being tightly held by appropriately mating surfaces of a needle holder, which is the third component, described further below. The needle and hub assembly, like the blood-collection tube, is supplied sterile, and furthermore the ends of the needles are physically guarded and kept sterile by a two-part sheath made of relatively rigid plastic. Each half of the sheath is placed over its respective end of the needle, the two halves meeting at the hub where a breakable seal is effected between the halves. The sheath half overlying the working (blood vessel puncturing) end of the needle also has a ribbed and grooved internal configuration which cooperatively mates with a similar ribbed and grooved outer surface of the hub, so that the sheath half can be used as a tool to rotate the needle/hub assembly to engage it with the needle holder. The third element is a needle holder which is essentially a plastic tube of slightly larger diameter than the blood collection tube, closed at one end except for a hole through which the stopper piercing portion of the blood collection needle can pass into the interior of the needle holder. The exterior of the closed end of the needle holder includes appropriately shaped surfaces for engaging the flanges or exterior threads of the needle hub, thereby holding the needle hub fast to the end of the needle holder when the needle hub is inserted therein and turned appropriately. Such engagement is accomplished in the one case by causing the radially extending hub flanges to be rotated so that they are wedged below overlying portions of the plastic holder, and in the other case by causing the hub external threads to be screwed into the corresponding internal threads of the plastic holder. Drawings and additional descriptions of the prior art apparatus are shown in U.S. Pat. No. 3,890.955, issued June 24, 1975 to Elliot.

The above described three-element apparatus is used in the following way. The seal between the two halves of the blood collection needle sheath is broken, and the half covering the stopper-piercing end of the needle is removed. Holding the blood collecting needle by the remaining sheath portion, the exposed end of the needle is inserted through the aperture in the end of the needle holder, and the sheath is turned to engage the needle hub with the needle holder. The stoppered end of the blood collection tube is inserted into the open end of the needle holder, but the stopper is not allowed to be pierced yet. The sheath covering the working end of the needle is removed, and the exposed needle, now securely attached to the needle holder, is inserted hypodermically into the blood vessel of the patient. While holding the needle stationary with respect to the patient, the blood collection tube is pushed up into the needle holder until the stopper is pierced by the end of the needle extending into the needle holder, whereby the needle is in communication with the evacuated interior of the blood collection tube, and blood is drawn through the needle into the tube.

If additional blood need be drawn, the blood collection tube can be withdrawn from the needle holder, leaving the needle in place in the blood vessel, and a fresh blood collection tube can be inserted into the needle holder and additional blood collected. When the required amount of blood has been withdrawn, the last blood collection tube is withdrawn from the needle holder, and the needle holder and needle are withdrawn from the patient in unison.

Since the needle and hub assemblies are disposable, but the needle holders are reusable, the needle must be disengaged from the needle holder so that the needle can be disposed of, and the needle holder preserved. In order to do this, the working end of the needle (which has just been withdrawn from the patient) must be resheathed so that the sheath can be used as a tool to disengage the needle hub from the needle holder, just as it was used in the first instance as a tool to engage the two.

Herein lies a grave danger to the medical technician. The act of resheathing a used needle is quite dangerous, as it is easy to miss and stick one's finger on the bloody needle. The technician risks contracting any blood borne disease the patient may have, such as hepatitis or AIDS. For this reason, public health authorities recommend that used needles not be resheathed. Nevertheless, for the sake of economics, resheathing is routinely practiced as the most expedient way to disengage the needle from the needle holder so that the needle holder, which has not been contaminated, can be reused.

The present invention avoids resheathing by a novel design of the needle holder wherein the means for engaging and disengaging the needle hub with respect to the needle holder is part of the needle holder itself, thereby making it unnecessary for the technician's hand to come anywhere near the sharp end of the used needle.

SUMMARY OF THE INVENTION

A needle holder for use with a blood collection needle having a first sharpened end and a second sharpened end and a hub intermediate the first and second ends of the needle, and an evacuated blood collection tube stoppered at one end by a rubber-like stopper includes a hollow tubular body configured for receiving at one end the hub of the blood collection needle and at the other end for receiving the blood collection tube. A sleeve is mounted to the hollow tubular body for rotation about the longitudinal axis of the tubular body, the sleeve being configured for selectively engaging and disengaging the needle hub with respect to the tubular body upon rotation of the sleeve with respect to the tubular body.

It is an object of the present invention to provide an improved blood collection needle holder which allows a used needle to be disengaged from the needle holder without resheathing the needle or otherwise exposing oneself to the sharp end of a used needle, which greatly reduces the risk of contracting disease from a contaminated needle which has been used to withdraw blood from a diseased patient.

Further objects and advantages will become apparent from the following descriptions.

DESCRIPTION OF THE PREFERRED EMBODIMENT

Figure 1:
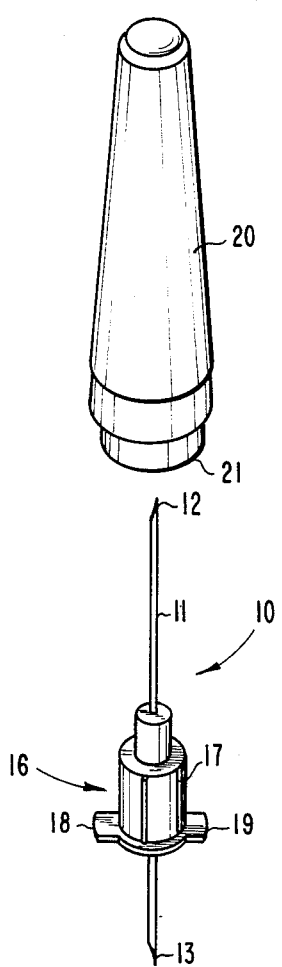
FIG. 1 is a perspective view of a prior art blood collection needle and one half of its associated protective sheath. The blood collection needle is useful in combination with the present invention.

For the purposes of promoting an understanding of the present invention, reference will now be made to the embodiment illustrated in the drawings and specific language will be used to describe the same. It is nevertheless to be understood that no limitation of the scope of the invention is thereby intended, the proper scope of the invention being indicated by the claims appended below and the equivalents thereof.

Referring in particular to FIG. 1, there is illustrated a typical prior art blood collection needle 10, which includes a hollow stainless steel cannula 11 which is sharpened at each end 12 and 13. The end 12 might be referred to as the working end, in that it is the portion of the cannula which is inserted hypodermically into the patient's blood vessel, while the end 13 might be referred to as the stopper-piercing end, in that it pierces the rubber stopper of the blood collection tube, as described in the Background of the Invention, above. Needle 10 also includes a hub 16 located intermediate the sharpened ends 12 and 13, but generally closer to the stopper piercing end 13. Hub 16 has a hollow outer aluminum shell with a plastic bushing therein (not visible in drawing), the outer aluminum shell being crimped about the bushing, thereby binding the hub 16 to the cannula 11. The outer surface of hub 16 is provided with a plurality of longitudinally oriented ribs 17, and two oppositely extending radial flanges 18 and 19, which are integral with the aluminum outer shell of the hub 16.

Also shown in FIG. 1 immediately above blood collection needle 10 is a plastic sheath 20 supplied with needle 10 and which fits over working end 12 of needle 10 and over a portion of hub 16. The interior surface of the bottom end 21 of sheath 20 is configured with a plurality of longitudinally oriented grooves which cooperatively engage ribs 17 of hub 16 to permit sheath 20 to be used as a tool for rotating hub 16 when attaching the needle 10 to prior art needle holders. While the needle holder of the present invention is configured to accept and be used with prior art needles of the type shown in FIG. 1, the use of sheath 20 as a rotating tool is obviated, as explained below.

Figure 2:
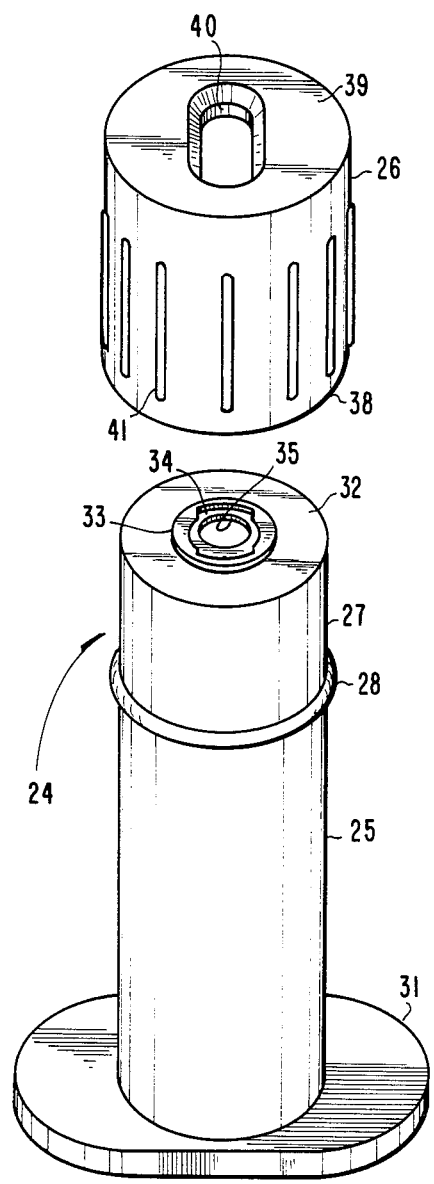
FIG. 2 is an exploded perspective view of a blood collection needle holder made in accordance with the present invention. The holder is shown exploded to more clearly show its two component parts, which are normally assembled together as shown in FIG. 3.

Referring to FIG. 2, there is shown the preferred embodiment of a needle holder 24 configured in accordance with the present invention. Holder 24 is comprised of two parts, a main body 25 and a sleeve 26, both of which are made of plastic. In FIG. 2, the two parts 25 and 26 are illustrated in an exploded arrangement, so that the details of main body 25 might be seen more clearly. When assembled together, sleeve 26 is received over the upper end 27 of main body 25 and is retained in place against axial displacement by an annular ridge 28, which engages a cooperating annular groove (not shown) on the inside surface of sleeve 26. As would be expected, rotation of sleeve 26 with respect to main body 25 is permitted by this arrangement, and is an important aspect of the functioning of holder 24.

Main body 25 is generally a hollow plastic tube having an inside diameter sufficiently large to receive a rubber-stoppered evacuated blood collection tube of the conventional type. The lower end of main body 25, which is open to receive the blood collection tube, includes finger flanges 31, and its upper end is partially closed by end wall 32. The upper surface of end wall 32 is provided with a raised boss 33 which includes an irregularly-shaped flat-bottomed depression 34, which as to its shape is formed to snugly receive from above the lower portion of hub 16 of needle 10, including flanges 18 and 19. The depth of depression 34 is slightly less than the vertical thickness of flanges 18 and 19. In the center of depression 34 is an aperture 35 for receiving end 13 of needle 10 therethrough, and aperture 35 is of sufficient size to freely receive therein also any extrusion of the plastic bushing of hub 16 which may extend below the bottom surfaces of flanges 18 and 19. This assures that there is no impediment to flanges 18 and 19 fully engaging the bottom of depression 34.

Sleeve 26 is generally a hollow plastic tube, open at its lower end 38, and having an internal diameter just large enough to fit over the upper end 27 of main body 25. Sleeve 26 is partially closed at its upper end by end wall 39, which end wall includes an oval aperture 40 therethrough. Oval aperture 40 is shaped so that hub 16, including flanges 18 and 19 can pass through it when flanges 18 and 19 are aligned with the long axis of the aperture, but flanges 18 and 19 cannot pass through oval aperture 40 when aligned at a right angle to the long axis of the aperture. The annular groove on the inside surface of sleeve 26, mentioned above, is located with respect to the inside surface of end wall 39 such that when sleeve 2 is assembled to main body 25 by pushing it down over the upper end 27 until annular ridge 28 snaps into the annular groove, the inside surface of end wall 39 is in tight abutting engagement with the upper surface of boss 33. Vertical ridges 41 on the outside surface of sleeve 26 are provided to aid in gripping sleeve 26 for the purpose of rotating it with respect to main body 25.

To use holder 24, sleeve 26 (having previously been assembled to main body 25) is rotated until oval aperture 40 is aligned with depression 34 (such alignment being shown in FIG. 2). Next, needle 10, with the lower end 13 unsheathed, is inserted through apertures 40 and 35, and flanges 18 and 19 are aligned so that they can pass through aperture 40 and be seated in depression 34. Sleeve 26 is next rotated 90° such that the interior surface of end wall 39 adjacent the long sides of oval aperture 40 override and overlie flanges 18 and 19. Since flanges 18 and 19 are slightly thicker than depression 34 is deep, and since the interior surface of end wall 39 abuts the top of boss 33, there will occur some flexing of the plastic and flanges 18 and 19 will thereby be securely compressed between the interior surface of end wall 39 and the bottom of depression 34, whereby needle 10 is held securely to holder 24 against both axial and rotational displacement.

When the time comes to remove needle 10 from holder 24, it may be accomplished simply by turning the whole assembly upside down over a waste needle container, and rotating sleeve 26 back to its original orientation, whereupon needle 10 will fall by force of gravity into the waste container. There is no need to resheath needle 10 to remove it, thereby avoiding the dangers mentioned above in the Background of the Invention. If desired, main body 25 and sleeve 26 can be provided with appropriate cooperating stops to restrict the range of relative motion to 90°, so that it may be determined by feel whether holder 24 is in the needle receiving/disgorging mode or in the needle retaining mode.

Figure 3:
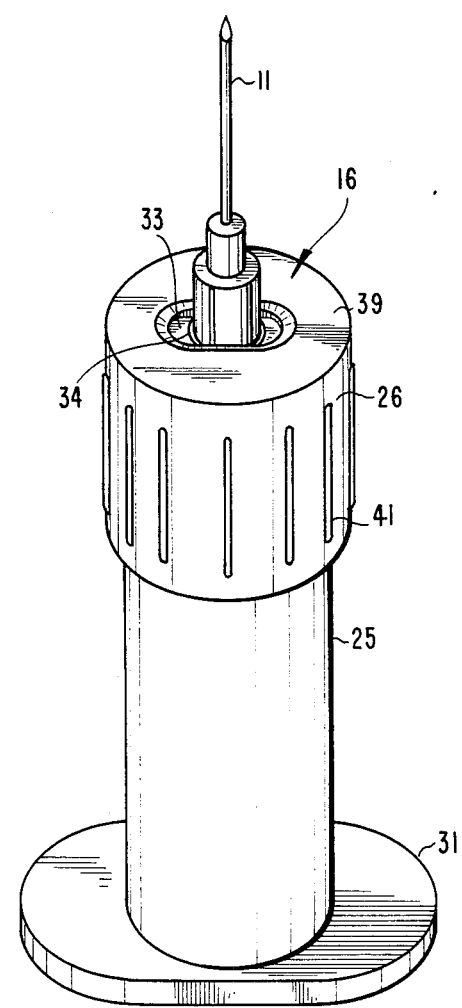
FIG. 3 is a perspective view of the needle holder of FIG. 2, shown assembled and holding the prior art needle of FIG. 1.

FIG. 3 shows holder 24 assembled together, with sleeve 26 rotated to hold needle 10 (via hub 16) in place.

While the preferred embodiment of the invention has been illustrated and described in some detail in the drawings and foregoing description, it is to be understood that this description is made only by way of example to set forth the best mode contemplated of carrying out the invention and not as a limitation to the scope of the invention which is pointed out in the claims below. Furthermore, the embodiment shown can be varied as desired, such as by eliminating the raised boss 33 and merely making end wall 32 of sufficient thickness to accommodate depression 34, in which case the exterior surface of end wall 32 would be configured in relation to the interior surface of end wall 39 as is the upper surface of boss 33 in the present embodiment.

What I claim is:

1. A needle holder for use with: a blood collection needle having a first sharpened end and a second sharpened end and a hub intermediate the first and second ends of the needle, and an evacuated blood collection tube stoppered at one end by a rubber-like stopper; comprising:

a main body including a hollow tube open at the first end and sized and configured to receive the stoppered end of said blood collection tube therein, said main body being partially closed at the second end by an end wall, the end wall defining an aperture for receiving therethrough the first end of the blood collection needle;

a sleeve received about the second end of said main body;

means for retaining said sleeve to said main body while permitting rotation of said sleeve with respect to said main body;

said sleeve and said main body including cooperative means for engaging and securing said needle hub to said main body in an orientation such that the first end of said needle is received through the aperture of the end wall of said main body, by rotating said sleeve with respect to said body, and also for disengaging and releasing said needle hub from said main body by rotating said sleeve with respect to said main body.

2. A needle holder for use with: a blood collection needle having a first sharpened end and a second sharpened end and a hub having radially extending portions intermediate the first and second ends of the needle, and an evacuated blood collection tube stoppered at one end by a rubber-like stopper; comprising:

a main body including a hollow tube open at the first end and sized and configured to receive the stoppered end of said blood collection tube therein, said main body being partially closed at the second end by an end wall, the end wall defining an aperture for receiving therethrough the first end of the blood collection needle;

a sleeve received about the second end of said main body;

means for retaining said sleeve to said main body while permitting rotation of said sleeve with respect to said main body;

said sleeve and said main body including cooperative means for engaging and securing said needle hub to said main body in an orientation such that the first end of said needle is received through the aperture of the end wall of said main body, by rotating said sleeve with respect to said body, and also for disengaging and releasing said needle hub from said main body by rotating said sleeve with respect to said main body, said cooperative means including a recess in the outer surface of the end wall of said main body sized and configured to receive the radially extending portions of said needle hub, and said sleeve including portions which alternately overlie and uncover said radially extending portions of said needle hub as said sleeve is rotated with respect to said main body.

3. The needle holder of claim 2, in which the sleeve includes an end wall on said sleeve adjacent the end wall of said main body, the end wall of said sleeve defining an oval aperture therethrough, the portions of the end wall of the sleeve adjacent the long sides of the oval aperture comprising the portions which alternately overlie and uncover said radially extending portions of said needle hub.

4. The needle holder of claim 3, in which the spacing between the portions of the end wall which overlie the radially extending portions of the needle hub and the recess of the end wall of the main body is such that the radially extending portions of the needle hub are compressed therebetween.

* * * * *